(12) United States Patent  (10) Patent No.: US 7,736,363 B2
Watanabe  (45) Date of Patent: Jun. 15, 2010

(54) HEMOSTATIC FORCEPS FOR ENDOSCOPE (75) Inventor: Hiroyoshi Watanabe, Tokyo (JP)

(73) Assignee: Olympus Corporation, Tokyo (JP)

( * ) Notice: Subject to any disclaimer, the term of this patent is extended or adjusted under 35 U.S.C. 154(b) by 982 days.

(21) Appl. No.: 10/890,754

(22) Filed: Jul. 14, 2004

(65) Prior Publication Data
US 2005/0049633 A1    Mar. 3, 2005

(30) Foreign Application Priority Data
Aug. 8, 2003    (JP) ............................. 2003-290285

(51) Int. Cl.
A61B 18/18    (2006.01)
(52) U.S. Cl. .............................. 606/52; 606/45; 606/46; 606/47; 606/48; 606/49; 606/50; 606/51; 606/205; 606/206; 606/207; 606/208
(58) Field of Classification Search ................ 606/205, 606/51, 206, 207, 208, 45–50, 52
See application file for complete search history.

(56) References Cited

U.S. PATENT DOCUMENTS

| 5,490,861 | A |   | 2/1996 | Kratsch et al. |   |
|---|---|---|---|---|---|
| 5,849,022 | A | * | 12/1998 | Sakashita et al. | 606/174 |
| 6,228,083 | B1 |   | 5/2001 | Lands et al. |   |
| 6,585,735 | B1 | * | 7/2003 | Frazier et al. | 606/51 |
| 6,964,662 | B2 | * | 11/2005 | Kidooka | 606/52 |
| 6,969,389 | B2 | * | 11/2005 | Kidooka | 606/51 |
| 7,255,697 | B2 | * | 8/2007 | Dycus et al. | 606/49 |
| 2002/0013595 | A1 |   | 1/2002 | Yamamoto |   |
| 2002/0188294 | A1 | * | 12/2002 | Couture et al. | 606/51 |
| 2002/0198525 | A1 | * | 12/2002 | Schulze et al. | 606/51 |
| 2003/0018331 | A1 | * | 1/2003 | Dycus et al. | 606/48 |
| 2003/0191464 | A1 | * | 10/2003 | Kidooka | 606/45 |
| 2003/0229344 | A1 | * | 12/2003 | Dycus et al. | 606/51 |
| 2004/0250419 | A1 | * | 12/2004 | Sremcich et al. | 29/861 |
| 2004/0254573 | A1 | * | 12/2004 | Dycus et al. | 606/51 |
| 2005/0075631 | A1 | * | 4/2005 | Kidooka | 606/51 |
| 2006/0052777 | A1 | * | 3/2006 | Dumbauld | 606/51 |
| 2006/0116675 | A1 | * | 6/2006 | McClurken et al. | 606/51 |
| 2007/0156139 | A1 | * | 7/2007 | Schechter et al. | 606/51 |
| 2007/0179499 | A1 | * | 8/2007 | Garrison | 606/51 |

FOREIGN PATENT DOCUMENTS

| JP | 10-151143 | 6/1998 |
|---|---|---|
| JP | 2001-522685 | 11/2001 |
| JP | 2002-65598 | 3/2002 |

* cited by examiner

Primary Examiner—Jing Ou
(74) Attorney, Agent, or Firm—Scully, Scott, Murphy & Presser, P.C.

(57) ABSTRACT

A hemostatic forceps for an endoscope has a support section for supporting the pair of clamp pieces and so that they can rotate and change their distal parts direction. The pair of clamp pieces and are formed in tapered shape so that widths of the pair of clamp pieces gradually decrease in a direction from a side of the support section to a side of the distal parts. Length of the pair of clamp pieces at arbitrary location along the direction from a side of the support section to the distal sides, times the width of the pair of clamp pieces at the same location, is set to be substantially constant.

5 Claims, 15 Drawing Sheets

HEMOSTATIC FORCEPS FOR ENDOSCOPE

BACKGROUND OF THE INVENTION

Priority is claimed on Japanese Patent Application No. 2003-290285, filed Aug. 8, 2003, the content of which is incorporated herein by reference.

FIELD OF THE INVENTION

The present invention relates to hemostatic forceps for an endoscope used together with a flexible endoscope.

DESCRIPTION OF RELATED ART

When excising an affected part growing on a mucous membrane, etc., of an internal face of a digestive organ, etc., while observing using a flexible endoscope, the affected part is clamped and cutoff by a high-frequency snare after cutting open, in advance, the mucous membrane around the affected part using an ultrasonic knife, etc.

As for a hemostatic forceps for an endoscope to stop bleeding occurring during a treatment, a hemostatic forceps for an endoscope which cauterizes and clots blood by applying high-frequency current to a clamped blood vessel, is well-known (for example, refer to FIG. 1 in Japanese Unexamined Patent Application, First Publication No. Hei 10-151143). The hemostat stops bleeding by clamping a blood vessel using its tubular shaped distal parts, and by cauterizes only an end of the blood vessel.

SUMMARY OF THE INVENTION

A hemostatic forceps for an endoscope of the present invention is a hemostatic forceps for an endoscope used together with a flexible endoscope. The hemostatic forceps for an endoscope includes an operation duct part inserted in a channel for a treatment tool formed in an insert unit of the endoscope; and a pair of clamp pieces connected to a distal side of the operation duct part, which is openable and closeable; and an operation part connected to a bottom side of the operation duct part, which controls open-and-closing action of the pair of clamp pieces. A support section supporting the pair of clamp pieces so that the pair of clamp pieces is rotatable and changeable in their distal parts direction, is provided to a bottom side of the pair of clamp pieces. Shapes of the pair of clamp pieces are formed so that widths of the pair of clamp pieces gradually decrease in a direction from a side of the support section thereof to a side of the distal parts thereof.

The hemostatic forceps for an endoscope including the above constitution can stop bleeding by firmly clamping and cauterizing a tissue, etc., using a narrow width portion formed on distal parts of a pair of clamp pieces, even in the case in which the tissue, etc., to be clamped is very small.

To stop bleeding of a tissue over a wide area, it is possible to clamp and cauterize it using a wide portion formed on the bottom side of the pair of clamp pieces. In this case, the tissue having a wide area can be cauterized by clamping it by the wide portion formed in the bottom side of the pair of the clamp pieces even in the case in which the tissue having a wide area has a spreading planar shape, because the distal portions of the pair of the clamp pieces can easily be inserted in the tissue.

It is possible to clamp a blood vessel, etc., in the more stable condition in the case in which the pair of clamp pieces approaches in a crossing direction toward the blood vessel, etc., because contact areas between the pair of clamp pieces and a tissue around the blood vessel increases compared to conventional ones having a tubular shape. It is also possible to minimize an area traversed by the pair of clamp pieces in a view area of the endoscope compared to conventional ones, because the distal parts of the pair of the clamp pieces are formed so that the shapes become narrower toward the distal side.

It is preferable that the length of the pair of clamp pieces at an arbitrary location along the direction from a side of the support section to a side of the distal parts, times the width of the pair of clamp pieces at the same location, be set to be substantially constant.

In this case, the pair of clamp pieces can clamp with equal pressure between at a side of the distal parts and at a side of the support section. Therefore, it is possible to cauterize the tissue, etc., in a uniform state.

It is preferable that concave portions be provided on center portions of clamp faces of the pair of clamp pieces, and the clamp faces be formed in a belt-like shape having constant width.

In this case, it is possible to have a constant cauterization width even in the case in which the tissue, etc., is clamped by arbitrary location on the clamp faces.

It is preferable that the pair of clamp pieces is closed so that a gap is formed between clamp faces of the pair of clamp pieces facing each other, and the clamp faces are placed parallel to each other.

In this case, it is possible to clamp the tissue, etc., with uniform pressure when the tissue, etc., is clamped between the clamp faces, because the clamp faces are placed in parallel to each other. It is also possible to close the pair of clamp pieces so that distal parts side of the clamp pieces firstly contact each other when the pair of clamp pieces is closed. Thus, the pair of clamp pieces can firmly clamp the tissue, etc., with the clamp faces even in the case in which the pair of clamp pieces has a manufacturing error.

It is preferable that each clamp face of the pair of clamp pieces have a plurality of grooves extending along a width direction of the clamp faces, formed at a constant pitch.

In this case, it is possible to firmly clamp the tissue, etc., by decreasing a possibility to have a slip between the clamp faces and the tissue, etc., more effectively, when the pair of clamp pieces clamps the tissue, etc. At the same time, it is possible to obtain uniform cauterization state even in the case in which the tissue, etc., is clamped by arbitrary location on the pair of clamp faces, because each area formed between the grooves on the clamp faces are equivalent.

It is preferable that concave portions be provided on center portions of clamp faces of the pair of clamp pieces, and that angles formed between an inner face of the concave portion and each of the clamp faces are set to be equal to or less than 90 degrees.

In this case, it becomes easier to catch the tissue, etc., by a contour line of the concave portion formed between the inner face of the concave portion and the clamp faces, when the pair of clamp pieces clamps the tissue, etc. Therefore, the pair of clamp pieces can firmly clamp the tissue, etc., by decreasing the possibility of slipping between the clamp faces and the tissue, etc.

It is preferable that maximum opening width be obtained when an opening angle between the pair of clamp pieces is substantially 60 degrees.

In this case, it is possible to improve the pair of clamp pieces having too small opening width which is not sufficient to clamp things thicker than a blood vessel. Therefore, the pair of clamp pieces can clamp and cauterize a blood vessel and a tissue around it at the same time.

DETAILED DESCRIPTION OF THE INVENTION

An embodiment of a hemostatic forceps for an endoscope according to the present invention will be explained below referring to the figures.

Figure 1:
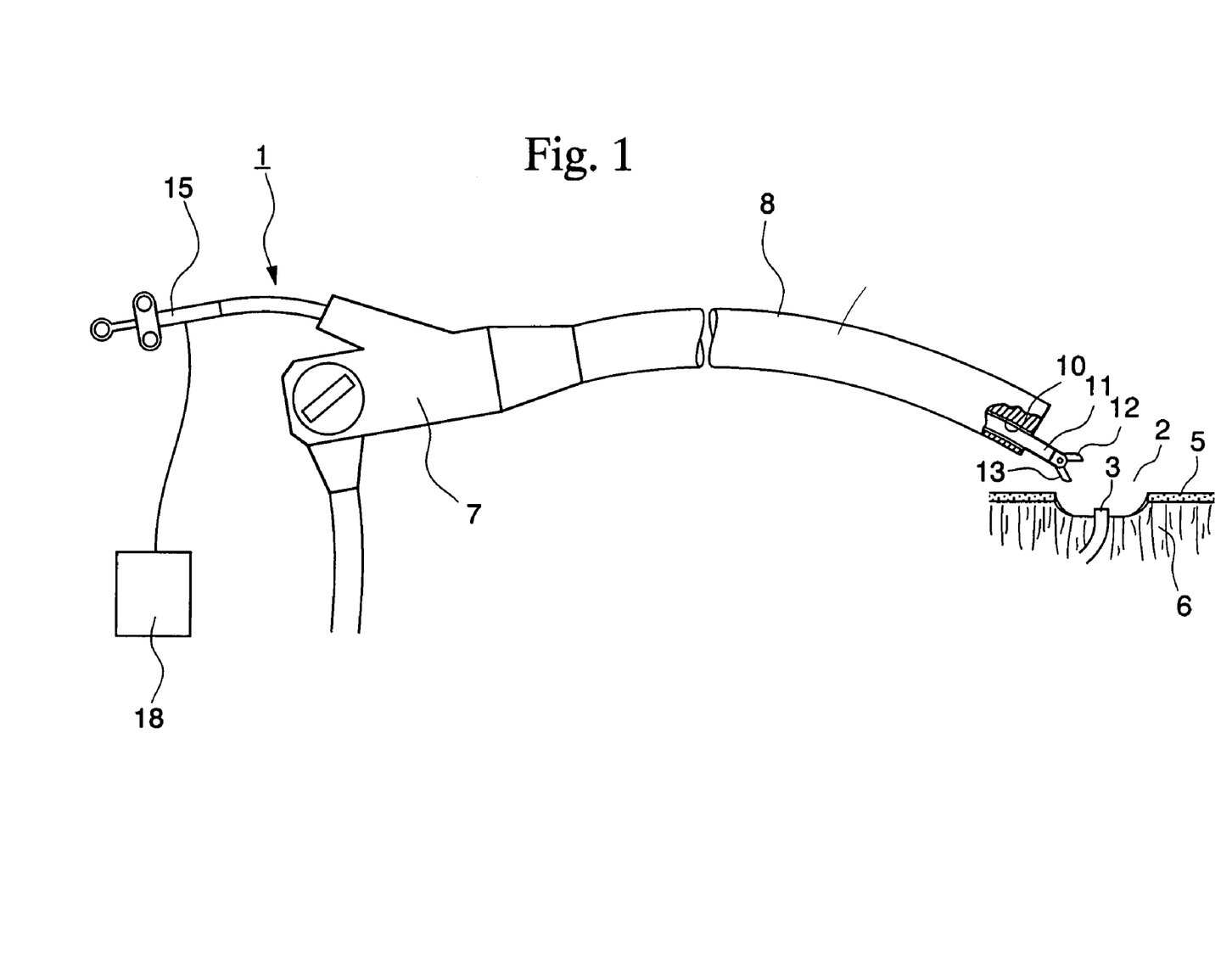
FIG. 1 is a block diagram showing an endoscope including hemostatic forceps for an endoscope according to an embodiment of the present invention.
Figure 2A:
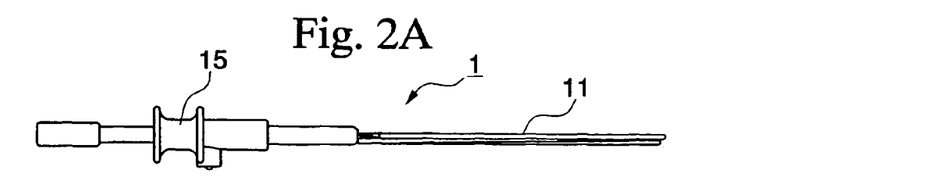
FIGS. 2A to 2F show the hemostatic forceps for an endoscope seen from six directions.
Figures 2B, 2C, 2D, 2E:
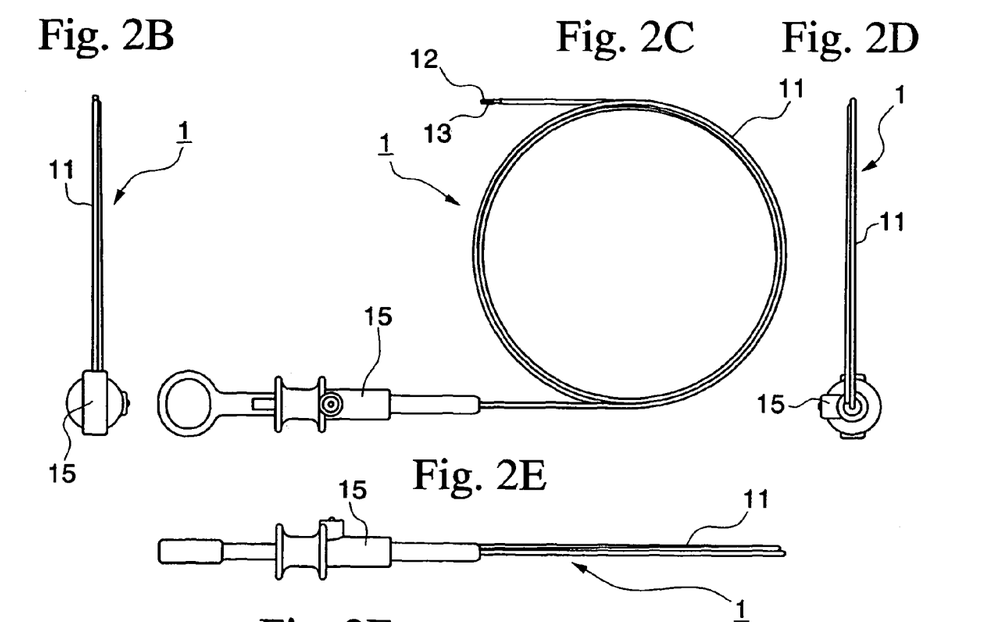
Figure 2F:
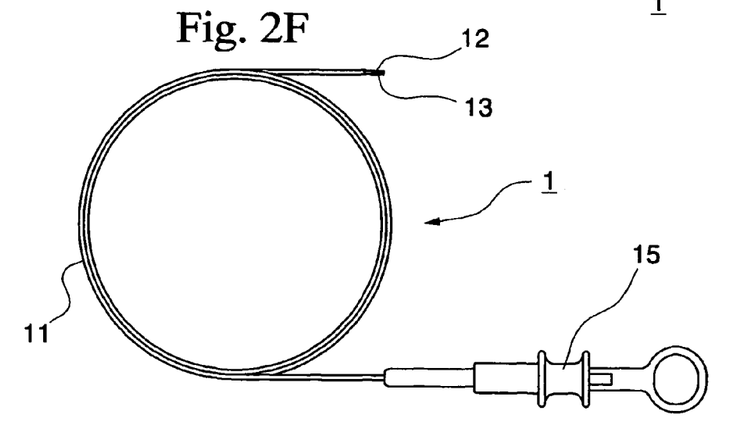

As shown in FIG. 1, a hemostatic forceps for an endoscope 1 according to the present embodiment can stop bleeding by cauterizing a blood vessel 3 exposed on an inner wall 2 of a cut-opened digestive organ, a mucous membrane 5, and a lower mucous membrane 6 thereabout, etc. As shown in FIGS. 1, and 2A to 2F, the hemostatic forceps for an endoscope 1 includes an operation duct part 11 inserted in a channel for a treatment tool 10 formed in an insert unit 8 of the endoscope 7, a pair of clamp pieces 12 and 13 connected to a distal side of the operation duct part 11, which can open and close, and an operation part 15 connected to a bottom side of the operation duct part 11, which controls the open-and-closing action of the pair of clamp pieces 12 and 13.

Figure 3:
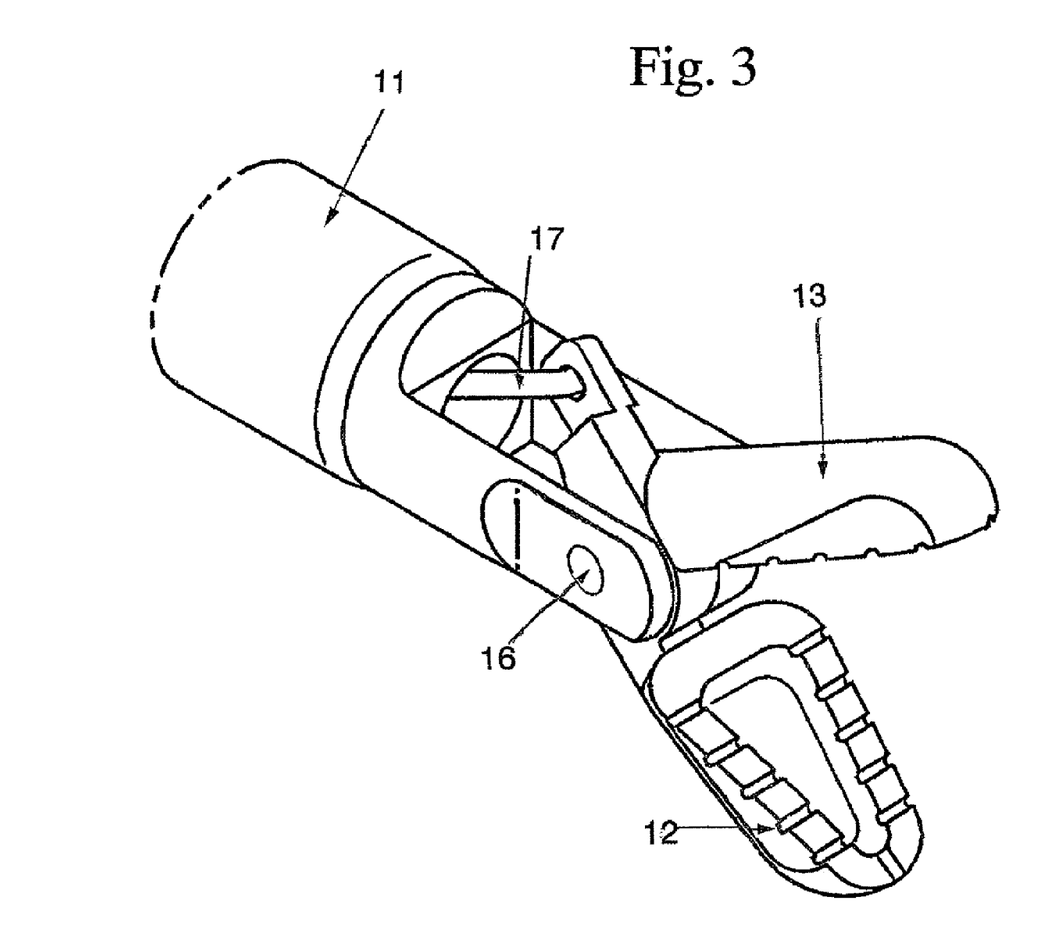
FIG. 3 shows a distal part of the hemostatic forceps for an endoscope in a perspective view.
Figures 4A, 4B, 4C:
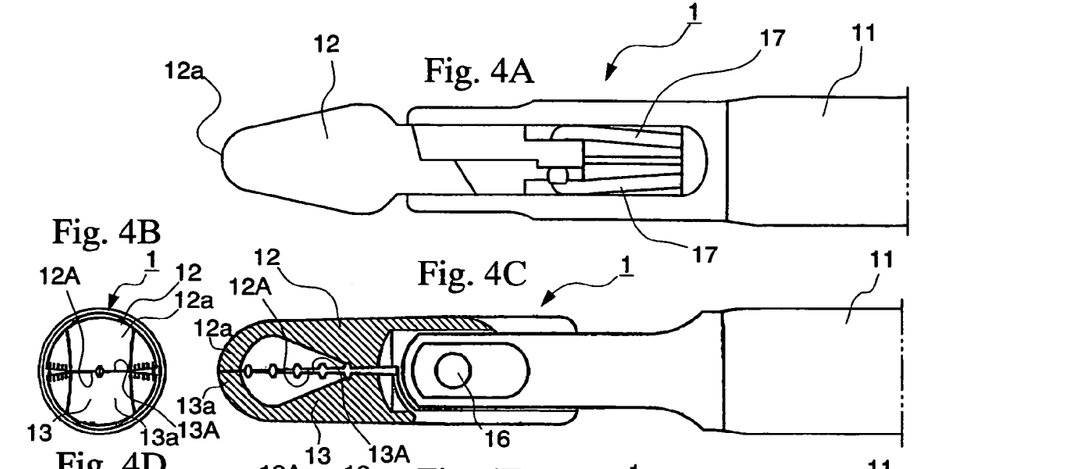
FIGS. 4A to 4H show each of open and closed states of a pair of clamp pieces of the hemostatic forceps for an endoscope seen from six directions.
Figures 4D, 4E, 4F, 4G, 4H:
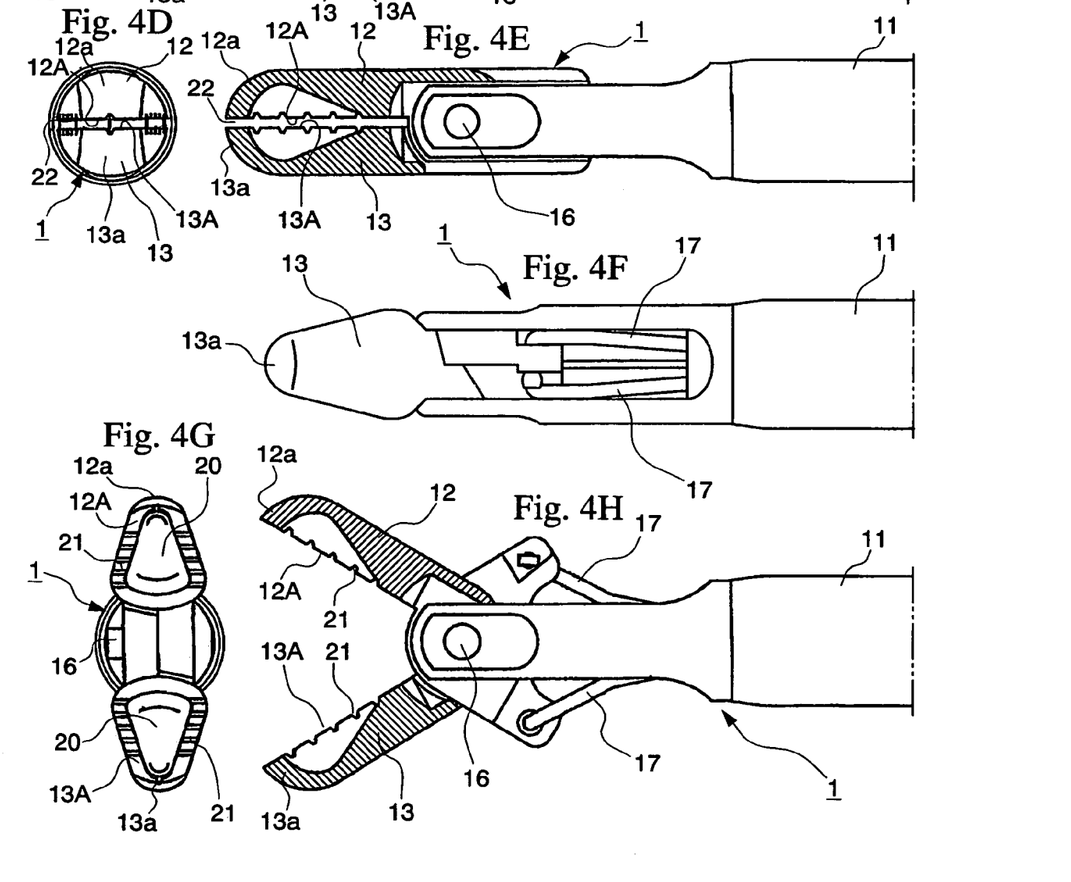
Figure 5A:
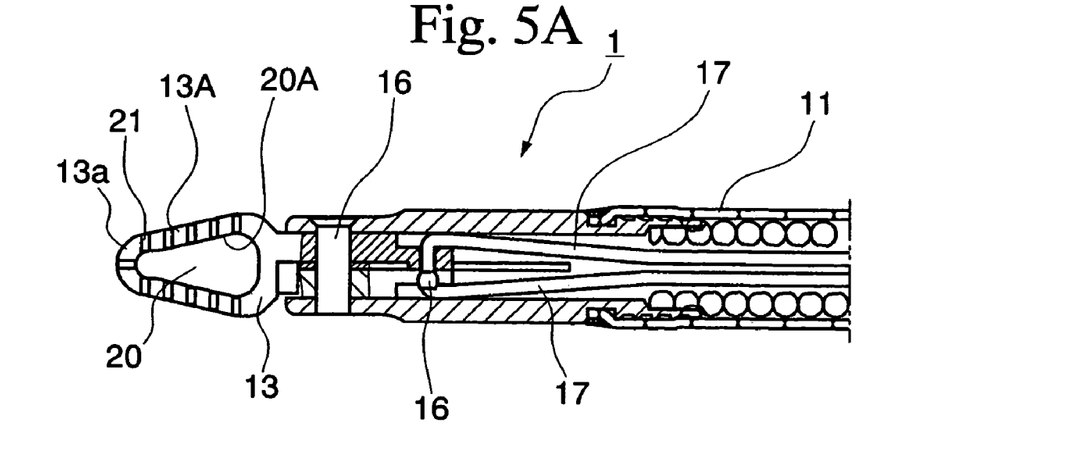
FIGS. 5A to 5C show each of open and closed states, in cross sectional view, of a pair of clamp pieces of the hemostatic forceps for an endoscope.
Figure 5B:
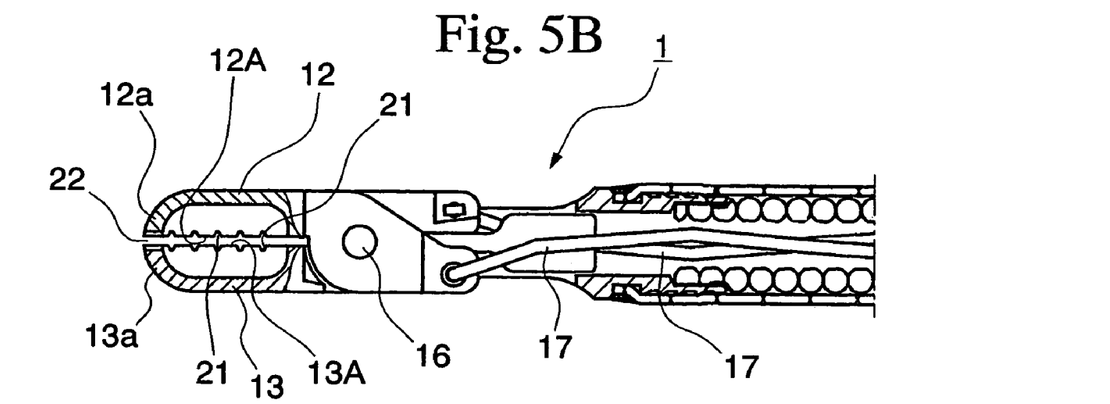
Figure 5C:
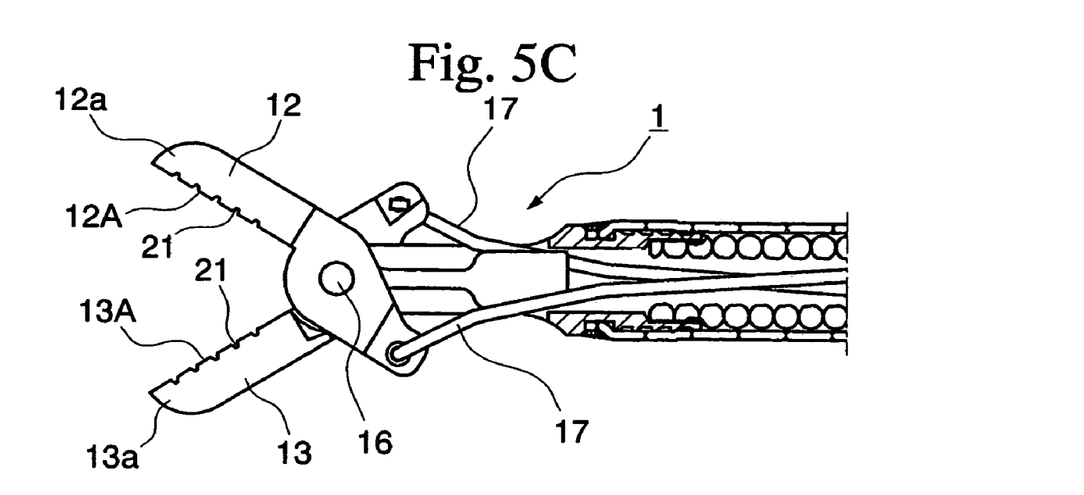

As shown in FIG. 3, a support section 16 supporting the pair of clamp pieces 12 and 13 so that the pair of clamp pieces 12 and 13 can rotate and change their distal parts direction, is provided to a bottom side of the pair of clamp pieces 12 and 13.

The pair of clamp pieces 12 and 13 opens and closes focusing on the support section 16 by pressing and pulling an operation wire 17 connected to the bottom side of the clamp pieces 12 and 13, and inserted inside of the operation duct part 11, using the operation part 15 (see FIG. 1).

An ultrasonic current from an ultrasonic power supply 18 is applied on the pair of clamp pieces 12 and 13 via the operation part 15 and the operation wire 17. Shape of the pair of clamp pieces 12 and 13 is formed so that the width of the pair of clamp pieces 12 and 13 gradually decreases in a direction from a side of the support section 16 to distal parts side 12a and 13a of the pair of clamp pieces 12 and 13. The shapes of the pair of clamp pieces 12 and 13 may adopt a tapered shape which becomes narrow in all circumferences.

In this case, length of the pair of clamp pieces 12 and 13 at an arbitrary location along the direction from a side of the support section 16 to a side of distal parts 12a and 13a of the pair of clamp pieces 12 and 13, times the width of the pair of clamp pieces 12 and 13 at the same location, is set to be almost constant.

Concave portions 20 are provided on each center portion of the clamp faces 12A and 13A, facing each other, of the pair of clamp pieces 12 and 13, and the clamp faces 12A and 13A are formed in a belt-like shape having constant width.

Each of the clamp faces 12A and 13A has a plurality of grooves 21 extending along a width direction of the clamp faces 12A and 13A, forming a constant pitch.

Figure 6A:
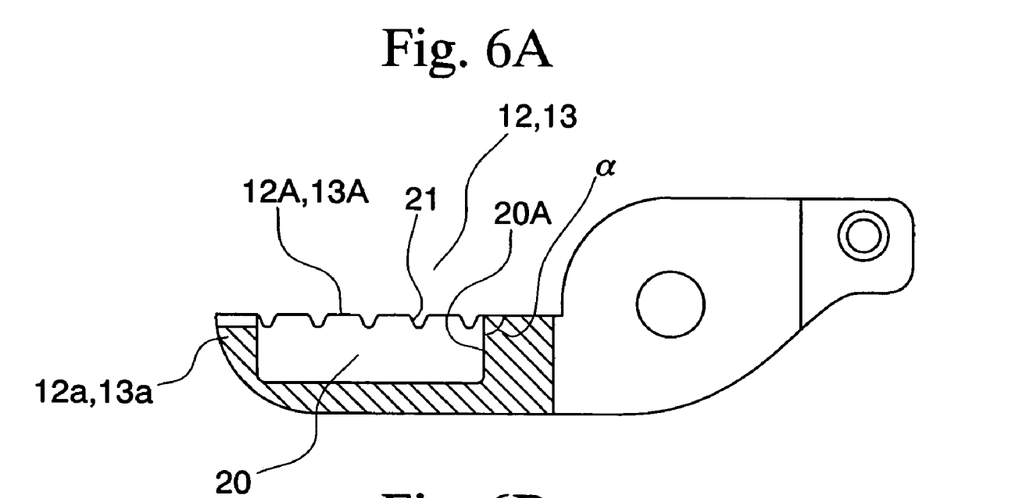
FIGS. 6A and 6B show the clamp piece of the hemostatic forceps for an endoscope, partially shown in cross sectional view.
Figure 6B:
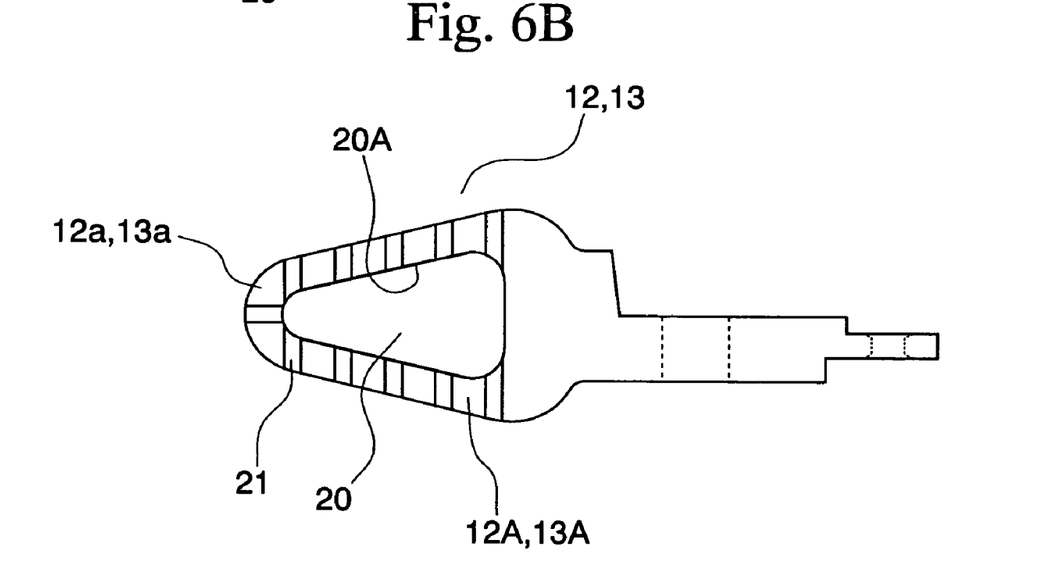

Angles formed between an inner face 20A of the concave portion 20 and each of the clamp faces 12A and 13A, denoted as α in FIG. 6A, are set to 90 degrees.

As shown in FIGS. 4A to 4H, 6A and 6B, the pair of clamp pieces 12 and 13 can close so that a gap 22 is formed between clamp faces 12A and 13A of the pair of clamp pieces 12 and 13 facing each other, and the clamp faces 12A and 13A are placed in parallel to each other.

Maximum opening width can be obtained when the opening angle between the pair of clamp pieces 12 and 13 focusing on the support section 16 is almost 60 degrees. In the present embodiment, the maximum opening width is set to about 5 mm which is almost the same length as a length between the support section 16 and distal parts of the pair of clamp pieces 12 and 13, and which can be obtained when the opening angle is about 62 degrees.

It is preferable to keep the maximum opening width of the pair of clamp pieces within the range of 3.5 mm to 6 mm to cauterize the blood vessel 3 including the lower mucous membrane 6 thereabout, etc.

Figure 7A:
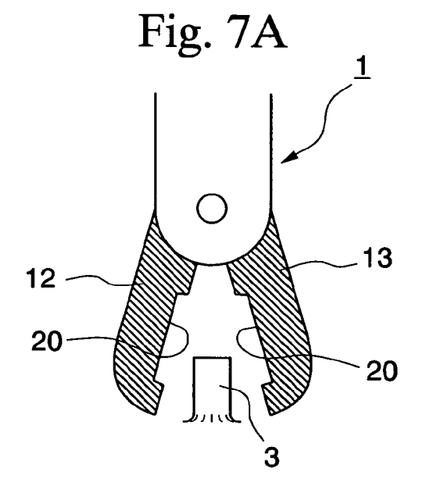
FIGS. 7A to 7D show a blood vessel, in plane view, clamped by a pair of clamp pieces provided in the hemostatic forceps for an endoscope.
Figure 7B:
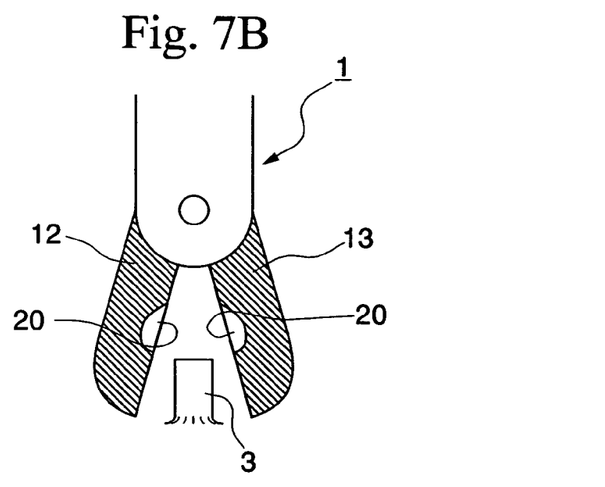

In the case in which depth of the concave portion 20 is shallow as shown in FIG. 7A, or in the case in which the area of the concave portion 20 is small and widths of the clamp faces 12A and 13A are wide, the blood vessel 3 will mainly be cauterized because the blood vessel 3 will directly contact to the concave portion 20 or the clamping faces 12A and 13A when clamping the blood vessel 3 to stop the bleeding and a mucous membrane. Therefore, the lower mucous membrane 6 thereabout, etc., will not be cauterized sufficiently.

Figure 7C:
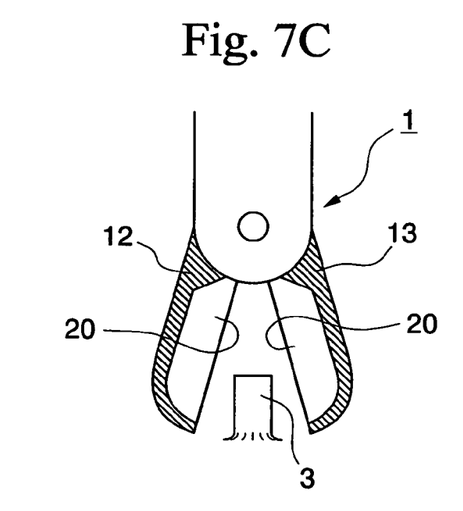
Figure 7D:
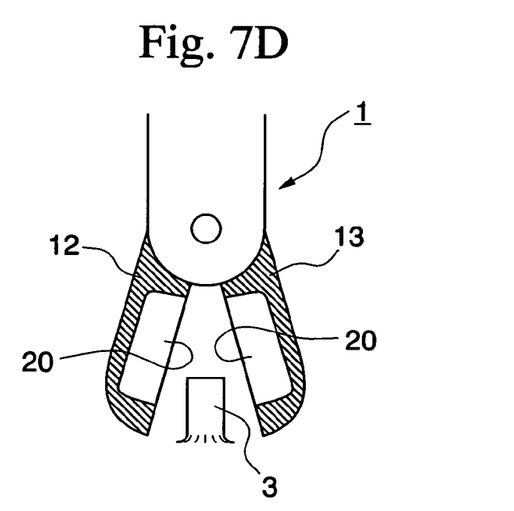

As shown in FIG. 7C, in the case in which an area of the concave portion 20 is too large and the each width of the clamp faces 12A and 13A is small, there is a case to cut-open the blood vessel 3, the lower mucous membrane 6, and etc., by the clamp faces 12A and 13A when clamping them. Therefore, it is preferable that the widths of the clamp faces 12A and 13A be 0.3 mm to 0.6 mm in particular, or ¼ to ⅛ of an external diameter of the pair of clamp pieces 12 and 13.

Next, use of the hemostatic forceps for an endoscope 1 will be explained.

Figure 8:
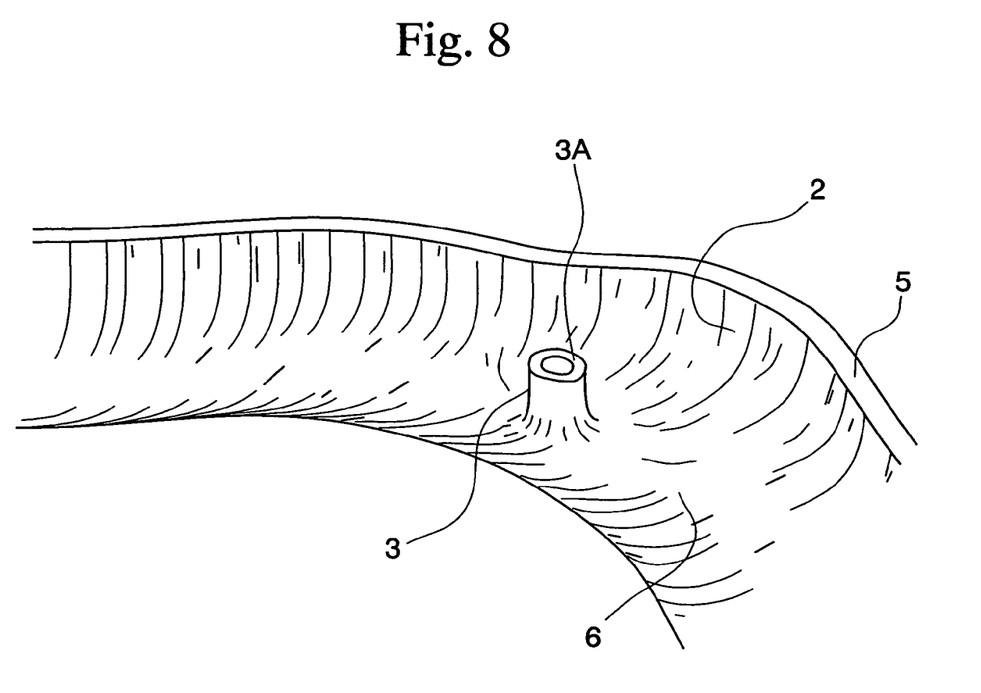
FIG. 8 shows a blood vessel at which bleeding is to be stopped its bleeding using the hemostatic forceps for an endoscope.

As shown in FIG. 8, in the case in which bleeding of the blood vessel 3 exposed and cut on the inner wall 2 of a cut-opened digestive organ is stopped, firstly, after inserting the insert unit 8 of the endoscope 7 until it reaches near the blood vessel 3, the hemostatic forceps for an endoscope 1 is inserted in the channel for a treatment tool 10, then is protruded from the distal part thereof.

Figure 9:
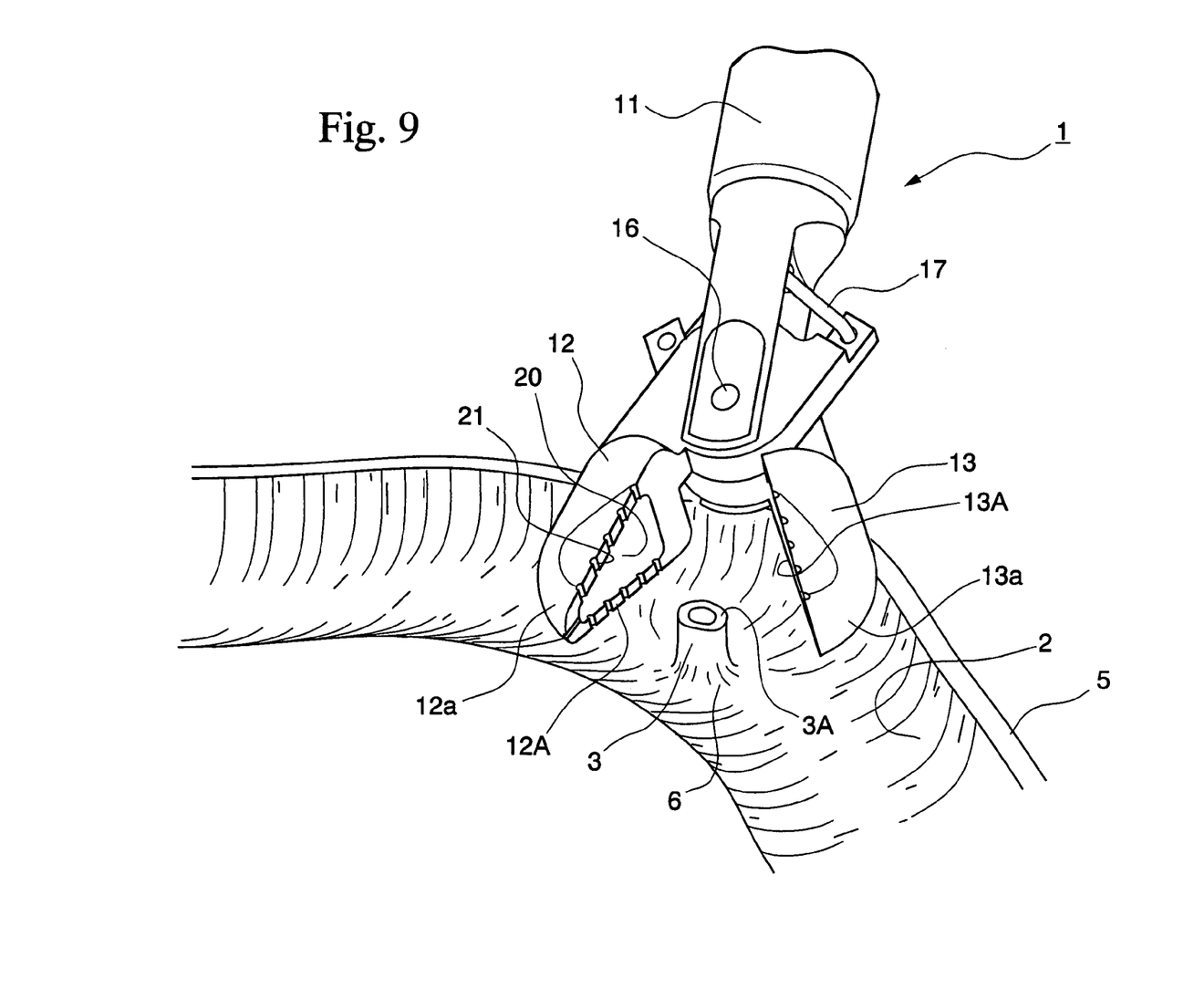
FIG. 9 shows the blood vessel before being clamped by the hemostatic forceps for an endoscope.

Then, as shown in FIG. 9, the pair of clamp pieces 12 and 13 is approached from the above of a cut face 3A of the blood vessel 3.

After approaching near the blood vessel 3, the pair of clamp pieces 12 and 13 is further approached toward the cut face 3A in a condition such that the pair of the clamp pieces 12 and 13 is opened to its maximum opening width by operating the operation part 15 and forwarding the operation wire 17. When the distal sides 12a and 13a of the pair of clamp pieces 12 and 13 contact to the inner wall 2 of a cut-opened digestive organ, the pair of clamp pieces 12 and 13 is closed by operating the operation part 15 and pulling the operation wire 17.

At this time, the clamp faces 12A and 13A clamp the blood vessel 3 including the lower mucous membrane 6 which is exposed around the blood vessel 3. On the other hand, a tip of the cut face 3A of the blood vessel 3 goes inside the concave portion 20, and will not contact to the clamp faces 12A and 13A.

Figure 10A:
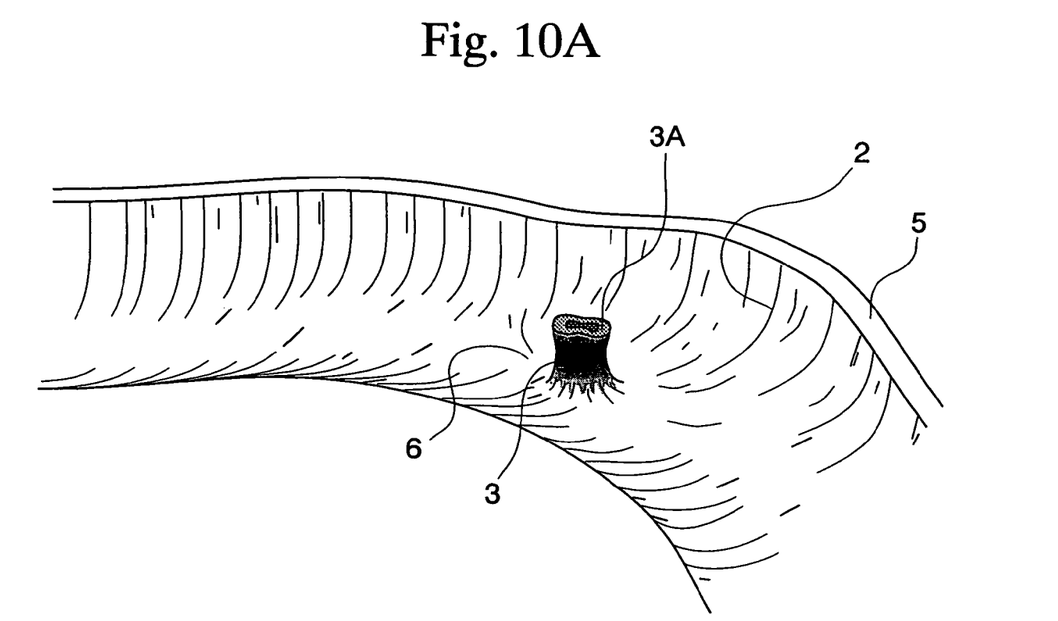
FIG. 10A shows the blood vessel at which bleeding is stopped using the hemostatic forceps for an endoscope of the present invention.
Figure 10B:
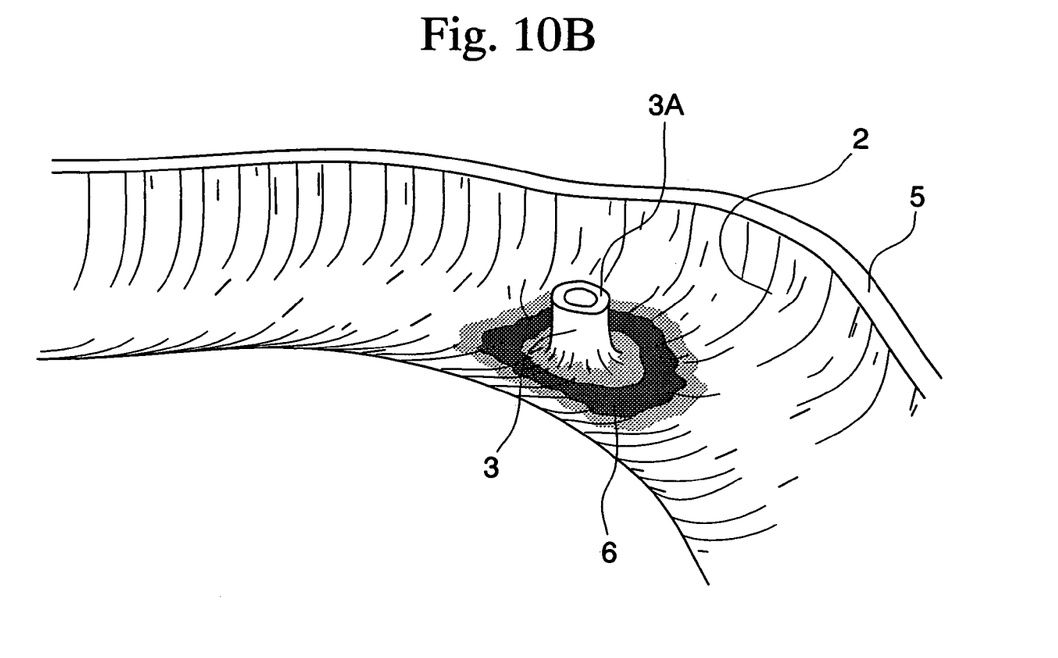
FIG. 10B shows the blood vessel at which bleeding is stopped using a conventional hemostatic forceps for an endoscope.
Figure 11:
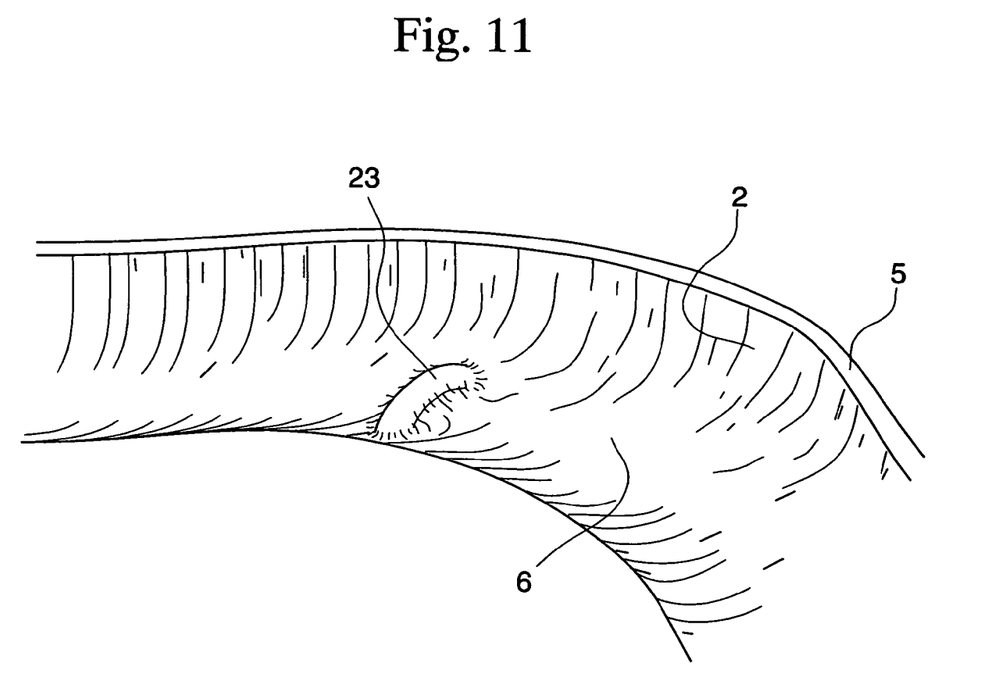
FIG. 11 shows another blood vessel at which bleeding is to be stopped using the hemostatic forceps for an endoscope.

Under this condition, when a high-frequency current is applied from the ultrasonic power supply 18, as shown in FIG. 10B, cauterization will be done for the lower mucous membrane 6 contacted to the clamp faces 12A and 13A, including the blood vessel 3, but except the near portion from the cut face 3A of the blood vessel 3. That is, the cauterization will not occur only at a near portion around the cut face 3A of the blood vessel 3 as shown in FIG. 10A, Next, how to stop bleeding of a blood vessel 23 crossing in the lower mucous membrane 6 of the inner wall 2 of a digestive organ, and has a possibility to happen bleed if cutting open of a mucous membrane is continued by a ultrasonic knife, etc., although it is still not bleeding, using the hemostatic forceps for an endoscope 1 in advance, will be explained.

Figure 12:
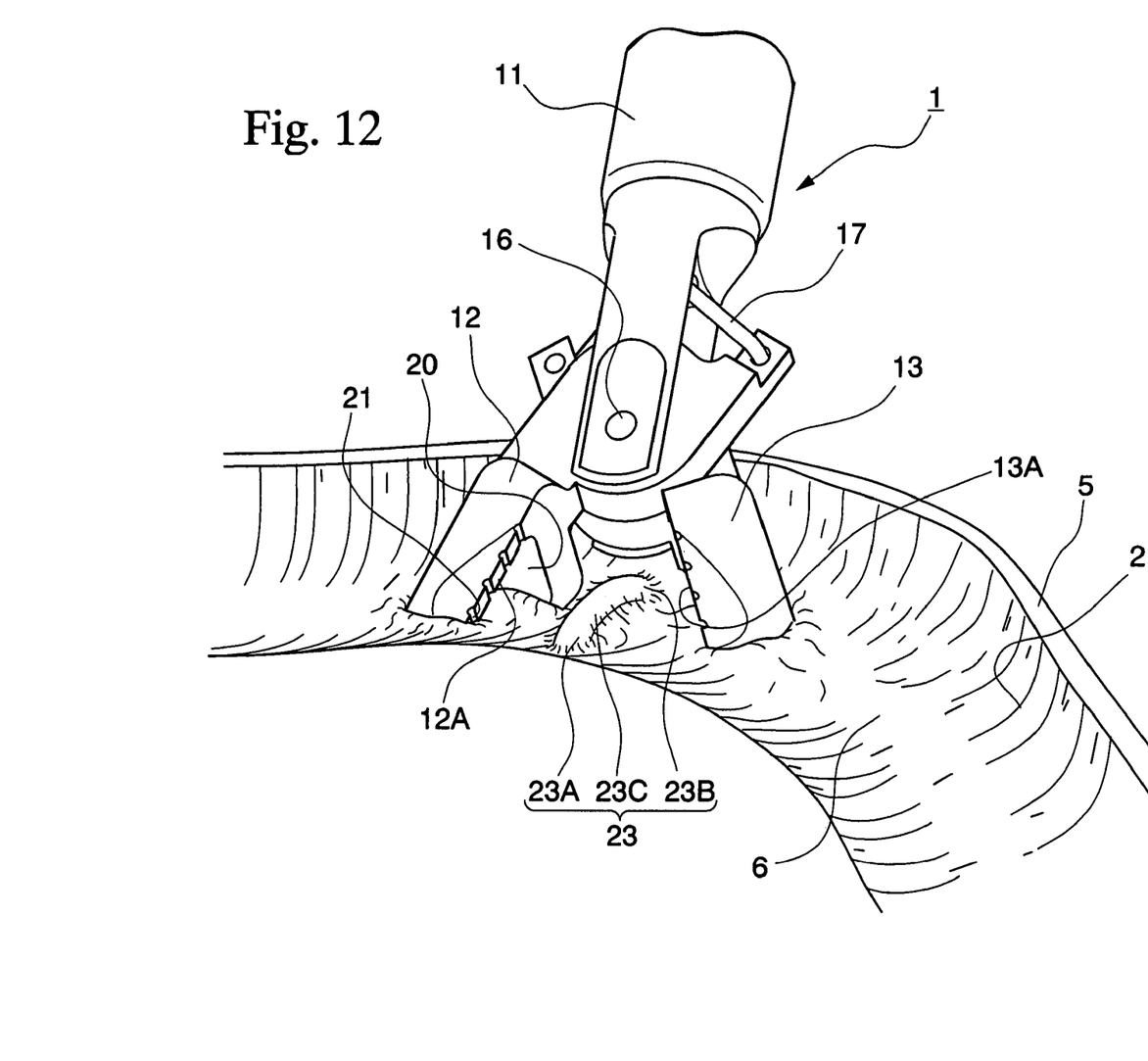
FIG. 12 shows a state before clamping the same blood vessel shown in FIG. 11 by the hemostatic forceps for an endoscope.

In this case, similarly as described the above, the pair of clamp pieces 12 and 13 is protruded from the distal part of the endoscope 7, then is opened to the maximum opening width. In this state, as shown in FIG. 12, the pair of clamp pieces 12 and 13 is inserted into the lower mucous membrane 6 around the blood vessel 23 from the distal sides 12a and 13a thereof to the bottom side thereof.

In this state, by closing the pair of clamp pieces 12 and 13, the clamp faces 12A and 13A formed on the bottom side of the pair of clamp pieces 12 and 13, and having a wide width will clamp the mucous membrane 5, the lower mucous membrane 6, and blood vessel portions 23A and 23B.

Figure 13:
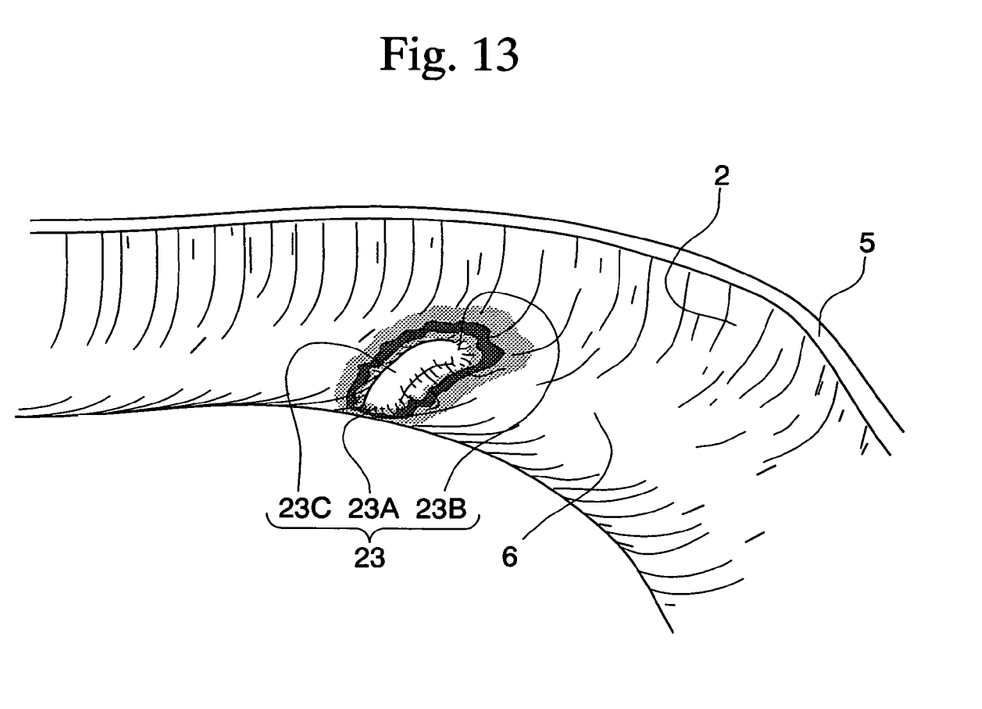
FIG. 13 shows the same blood vessel shown in FIG. 11 at which bleeding is stopped using the hemostatic forceps for an endoscope.

In this state, by applying the high-frequency current in a similar manner as described above, as shown in FIG. 13, a portion clamped by the clamp faces 12A and 13A is cauterized in belt shape having the same width as the width of the clamp faces 12A and 13A, although a blood vessel portion 23C of the blood vessel 23 going inside the concave portion 20 and not being clamped by the clamp faces 12A and 13A will not be cauterized. Then the blood vessel portions 23A and 23B cauterized will stop the bleeding, After that, even when the not cauterized blood vessel portion 23C is cut opened by an ultrasonic knife, etc., bleeding can be minimized because the blood portions 23A and 23B are cauterized.

According to the hemostatic forceps for an endoscope 1, in the case in which the blood vessel 23, etc., to be clamped is too small, it is possible to firmly clamp it using clamp faces 12A and 13A formed on the distal sides 12a and 13a having narrow width, stopping the bleeding.

In the case in which a portion to be cauterized has a large area, it is possible to clamp the blood vessel 23, etc., using the bottom sides which are broad, of the clamp pieces 12 and 13. In this case, even when a portion to be cauterized is a tissue spreading in a plane shape like the inner wall 2 of a digestive organ, it is possible to stop the bleeding by applying broad portions formed on the bottom side of the clamp pieces 12 and 13 on a surface of the lower mucous membrane 6, then cauterizing it, because the distal sides 12a and 13a can be easily inserted in the lower mucous membrane 6.

In this case, it is possible to clamp the blood vessel 23 including the lower mucous membrane 6 around it, etc., without mashing the cut face 3A by the clamp faces 12A and 13A, because the concave portion 20 is formed on each of the center portion of the clamp faces 12A and 13A, and a distal part portion of the blood vessel 23 can get inside the concave portion 20.

Figure 14:
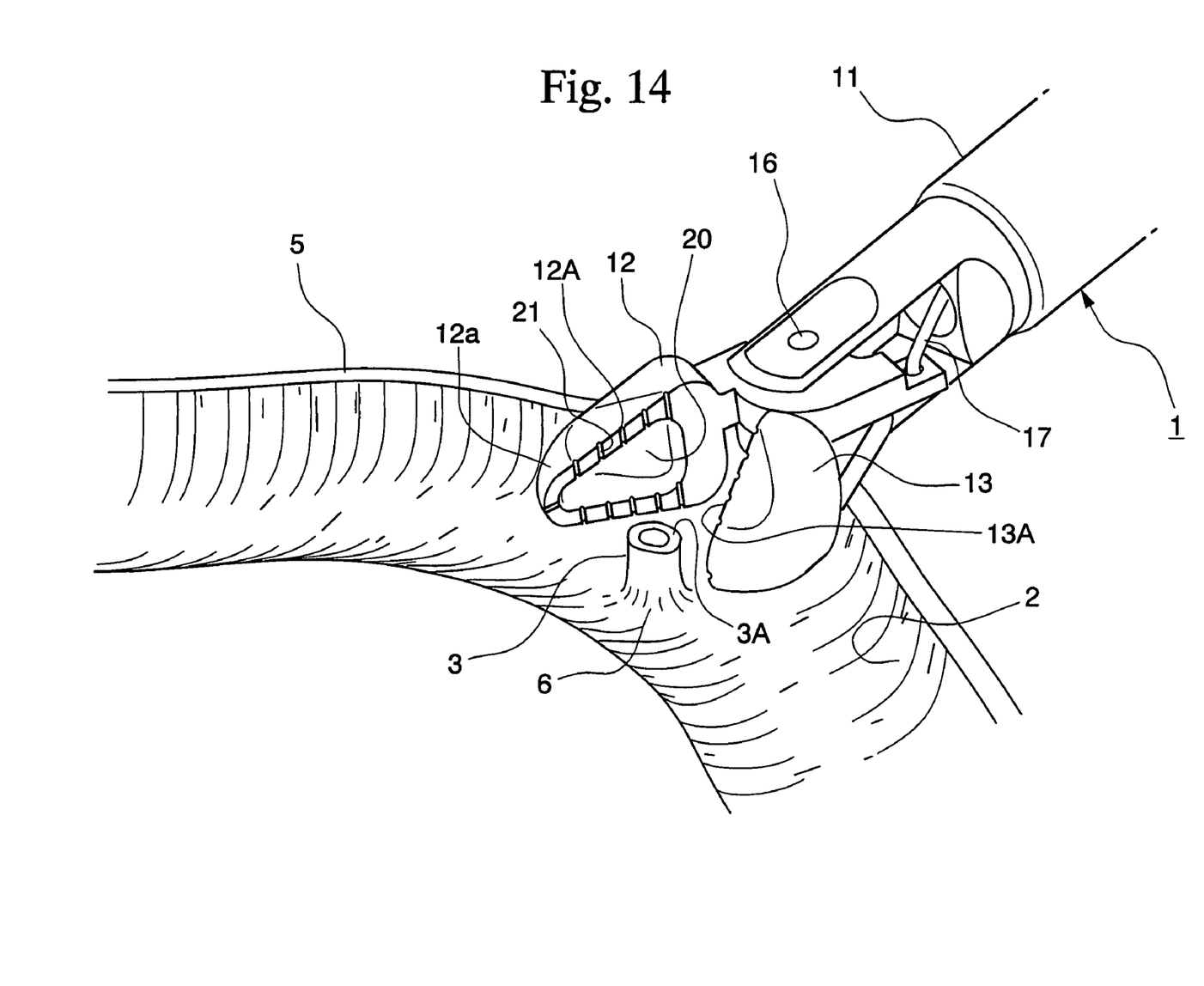
FIG. 14 shows a blood vessel before being clamped by the hemostatic forceps for an endoscope seen from another direction.

It is possible to clamp a blood vessel 3, in more stable condition in the case in which the pair of clamp pieces 12 and 13 approaches in a crossing direction toward the blood vessel 3 as shown in FIG. 14, because contact areas between a circular edge portion of the pair of clamp pieces 12 and 13 and the inner wall 2 of a digestive organ increases compared to a conventional ones having a tubular shape.

During the operation, it is also possible to minimize an area traversed by the pair of clamp pieces 12 and 13 in a view area in front of the insert unit 8 of the endoscope 7 compared to conventional ones, because the distal parts of the pair of the clamp pieces 12 and 13 are formed so that the shapes become narrower toward the distal side.

The pair of clamp pieces 12 and 13 can clamp with equivalent pressure between at the distal side and at the bottom side, because length of the pair of clamp pieces 12 and 13 at arbitrary location along the direction from a side of the support section 16 to the distal sides 12a and 13a, times the width of the clamp faces 12A and 13A at the same location is set to be constant. Therefore, it is possible to cauterize a tissue such as the blood vessel 3, etc., in a uniform state at any location.

In the present embodiment, the concave portions 20 are provided on center portions of the clamp faces 12A and 13A, and the clamp faces 12A and 13A are formed in a belt-like shape, and the grooves 21 are formed on the clamp faces 12A and 13A in constant pitch. Therefore, it becomes possible to obtain a uniform cauterization state because each area formed between the grooves 21 on the clamp faces 12A and 13A are equivalent and clamping pressure at any location can be constant.

In the present embodiment, the angle α which is a supplementary angle of an angle formed between an inner face 20A of the concave portion 20 and each of the clamp faces 12A and 13A are set to equal or less than 90 degrees. Therefore, in the case in which the pair of clamp pieces 12 and 13 clamps a tissue such as the blood vessel 3 or the lower mucous membrane 6, it becomes easier to catch the tissue by a contour line of the concave portion 20, because a portion of the blood vessel 3 contacting to the inner face 20A of the concave portion 20 can be decreased compared to the case in which the angle α is equal or over the 90 degrees. Furthermore, in the case in which the pair of clamp pieces 12 and 13 clamps the lower mucous membrane 6, it is possible to firmly clamp it so as to decrease the probability of having a slip between the clamp faces 12A and 13A, and the inner wall 2 of a digestive organ more effectively, because the grooves 21 are formed on the clamp faces 12A and 13A.

Figure 15A:
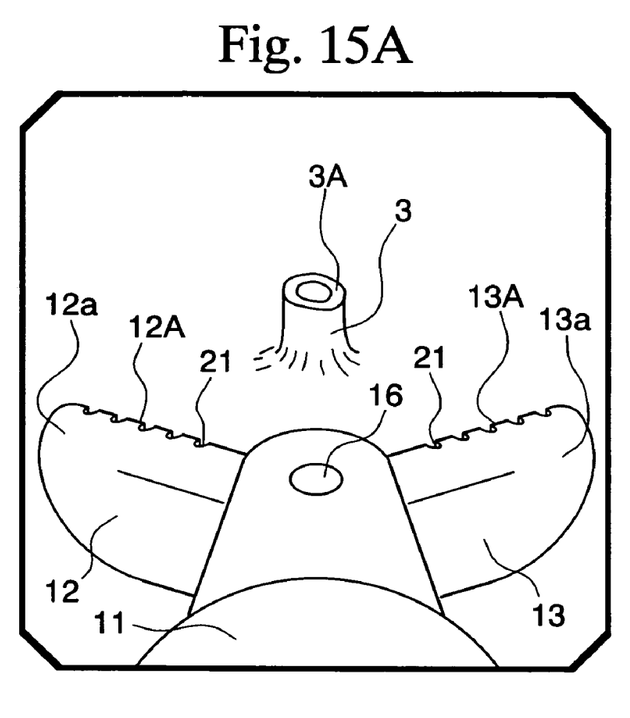
FIGS. 15A and 15B show observation screens showing an endoscope in which the pair of clamp pieces is opened for clamping a blood vessel using the hemostatic forceps for an endoscope.
Figure 15B:
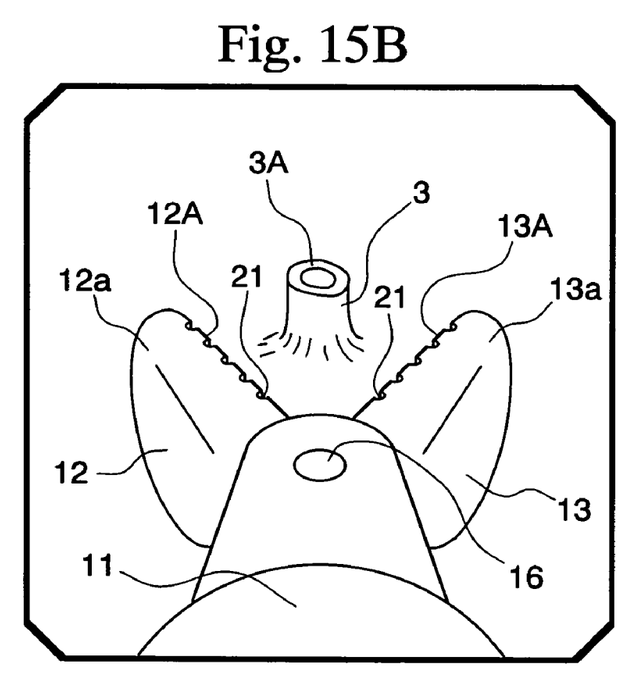

It is possible to clamp and cauterize not only the blood vessel 3 but also including the lower mucous membrane 6 around it at the same time, because the maximum opening width is set so that it can be obtained when the opening angle between the pair of clamp pieces 12 and 13 centering on the support section 16 are almost 60 degrees. In this case, it becomes easier to aim near the blood vessel 3 to be clamped, because opening state of the pair of clamp pieces 12 and 13 will not be as shown in FIG. 15A, but will be as shown in FIG. 15B.

When closing the pair of clamp pieces 12 and 13 until the clamp faces 12A and 13A contact each other, clamping the blood vessel 3, etc., applying excessive pressure can be avoided by the gap 22 formed between the pair of clamp pieces 12 and 13.

When closing the pair of clamp pieces 12 and 13 completely, the pair of clamp pieces 12 and 13 can begin to close from the distal sides 12a and 13a by contacting the clamp faces 12A and 13A with each other. Therefore, even when the pair of clamp pieces has some manufacturing errors, the pair of clamp pieces 12 and 13 can firmly clamp the blood vessel 3, etc., by the clamp faces 12A and 13A, avoiding the state that distal sides 12a and 13a are opened.

According to the present invention described above, bleeding can be firmly stopped by clamping and cauterizing the blood vessel 3 to stop the bleeding, including tissue therearound.

While preferred embodiment of the invention has been described and illustrated above, it should be understood that this is exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, in the present embodiment described the above, although the angle formed between the inner face 20A of the concave portion 20 and each of the clamp faces 12A and 13A are set to equal to 90 degrees, the angle is not limited only to 90 degrees, and an angle less than 90 degrees can also be adopted. By adopting such an angle, the contour line of the concave portion 20 will form a sharp edge. Thus, a tissue such as the blood vessel 3, etc., can be clamped by the clamp faces 12A and 13A, avoiding a slip between them.

What is claimed is:

1. A hemostatic forceps for an endoscope used together with a flexible endoscope, comprising:

an operation dud part inserted in a channel for a treatment tool formed in an insert unit of the endoscope;

a pair of clamp pieces connected to a distal side of the operation duct part, which is openable and closeable; and an operation part connected to a bottom side of the operation dud part, which controls opening-and-closing action of the pair of clamp pieces, wherein a support section supporting the pair of clamp pieces so that the pair of clamp pieces is rotatable and changeable in their distal directions, is provided to a bottom side of the pair of clamp pieces;

clamp faces of the pair of clamp pieces facing each other can be parallel to each other while having a gap therebetween over the entire faces even when the clamp faces are not completely closed;

shapes of the pair of clamp pieces are fanned so that widths of the pair of clamp pieces gradually decrease in a direction from a side of the support section thereof to a side of distal parts of the pair of the clamp pieces;

a length of the pair of clamp pieces at an arbitrary location along the direction from the side of the support section to the side of the distal parts, times a width of the pair of clamp pieces at the same location, is set to be sufficiently constant; and in a state where the pair of clamp pieces is completely closed, width of a gap formed between peripheral edges of the clamp faces of the pair of clamp pieces gradually increases throughout the entire clamp faces from the side of the distal parts to the side of the support section, and distal ends of the clamp faces contact with each other so that there is no space between the distal ends of the clamp faces.

2. The hemostatic forceps for an endoscope according to claim 1, wherein concave portions we provided on center portions of clamp faces of the pair of clamp pieces; and the clamp faces are formed in a belt-like shape having constant width.

3. The hemostatic forceps for an endoscope according to claim 1, wherein each clamp face of the pair of clamp pieces has a plurality of grooves extending along a width direction of the clamp faces, formed at a constant pitch.

4. The hemostatic forceps for an endoscope according to claim 1, wherein concave portions are provided on center portions of clamp faces of the pair of clamp pieces; and angles formed between an inner faces of the concave portions and each of the clamp faces are set to be equal to or less than 90 degrees.

5. The hemostatic forceps for an endoscope according to claim 1, wherein maximum opening width is obtained when an opening angle between the pair of clamp pieces is substantially 60 degrees.

* * * * *